United States Patent [19]

Garde

[11] Patent Number: 4,583,546
[45] Date of Patent: Apr. 22, 1986

[54] BLOOD LOSS MONITOR

[76] Inventor: Patria P. Garde, 61 Laurel La., Hammonton, N.J. 08037

[21] Appl. No.: 553,291

[22] Filed: Nov. 18, 1983

[51] Int. Cl.⁴ ............................................. A61F 13/16
[52] U.S. Cl. .................... 128/638; 604/361; 128/639
[58] Field of Search ............... 128/638, 639, 138 A, 128/736, 742, 771, 635, 419 R; 340/604; 604/358, 361

[56] References Cited

U.S. PATENT DOCUMENTS

| | | | |
|---|---|---|---|
| 2,907,841 | 10/1959 | Campbell | 128/138 A |
| 3,832,993 | 9/1974 | Clipp | 128/638 |
| 4,231,370 | 11/1980 | Mroz et al. | 604/361 |
| 4,327,731 | 5/1982 | Powell | 604/361 |
| 4,333,477 | 6/1982 | Chervitz | 128/736 |

Primary Examiner—Edward M. Coven
Attorney, Agent, or Firm—Steele, Gould & Fried

[57] ABSTRACT

A blood loss monitor which signals blood loss and profuse bleeding utilizing the physical characteristics of blood to indicate bleeding and wetness in different levels of a pad.

17 Claims, 3 Drawing Figures

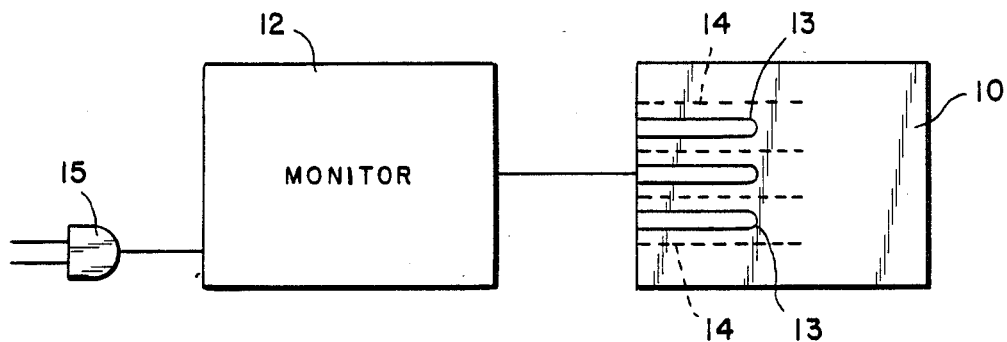
FIG. 1.
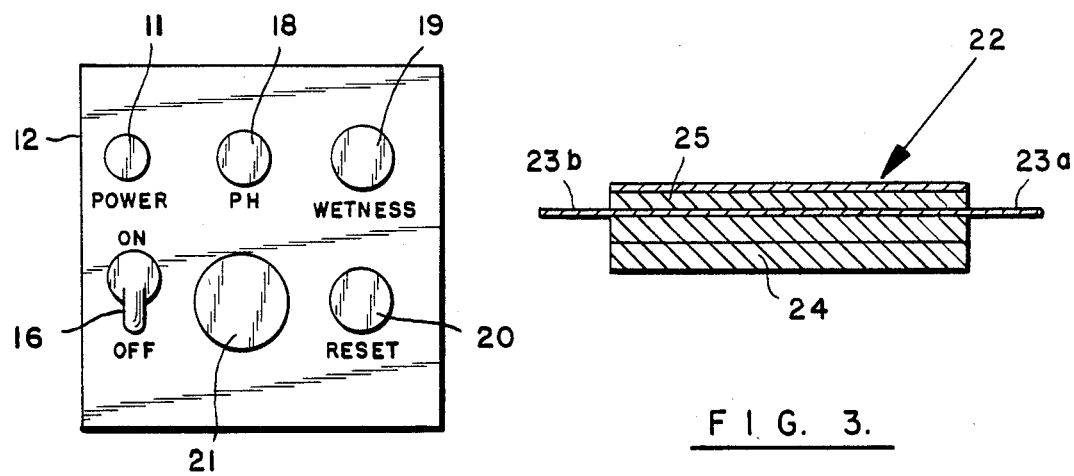
FIG. 2.
FIG. 3.

BLOOD LOSS MONITOR

BACKGROUND OF THE INVENTION

This invention relates to a blood loss monitor and is particularly concerned with a monitor adapted for use with a patient who has been subjected to major surgery. More particularly, the present invention relates to a monitor which will signal profuse blood loss by a patient which has undergone major surgery and leaves the patient vulnerable to undetected blood loss as a result of inadvertent opening of a wound when the patient is asleep or unconscious.

One of the objects of the invention is to provide a monitor arranged to give a signal under certain conditions resulting from a measurable blood condition such as the measurement of blood glucose, pH, or a change in a degree of wetness which occurs upon the loss of blood from a patient.

More particularly, the invention contemplates the provision of a monitor giving a warning signal upon the occurrence of any one of several events resulting from a bleeding problem. Thus, the monitor according to the present invention gives a warning signal in the event that a patient is profusely bleeding and not merely occasionally oozing blood as a result of a temporary occurence. The monitor is also arranged to give a signal after intermittent bleeding which may be sufficient to cause a problem or crisis in the patient.

It is a further object of the invention to provide for manual resetting of the monitor at least with relation to the actuation or energization of the warning system following the occurrence of a determination of the degree of bleeding.

In accordance with another aspect of the invention, the monitor is arranged to give a warning signal when a predetermined pH value or blood glucose and be ascertained.

In accordance with another aspect of the invention, the monitor is arranged to give a warning signal with the occurrence of two separate events.

SUMMARY OF THE INVENTION

The monitor of the present invention is also arranged so that in the event of the failure of a power supply, a warning signal is given.

In the preferred arrangement of the invention the warning signal occurs at the time a predetermined change of pH can be measured or blood glucose can be measured. The measurement in the change of pH or a blood glucose measurement occurs when a contact is made because of wetness and because of the presence of sufficient blood to cause a measurement in the pH reading or of a glucose meter. In each event a different warning signal is actuated--immediately in response to bleeding by the patient.

For the various purposes previously referred to, both audible and visual signals may be employed in parallel, so that doctors, nurses or other attendants using the equipment may be apprised of changes either "by ear" or by observing the visual signals.

How the foregoing objects and advantages will be attained will be clear from the following description referring to the accompanying drawing in which:

BRIEF DESCRIPTION OF THE DRAWING

FIG. 1 is a diagrammatic block diagram representing the general manner of association of a monitor and a blood loss indicating pad according to the present invention;

FIG. 2 is a top view of one type of monitor used in connection with the invention, this view primarily illustrating the main panel and controls of the instrument; and FIG. 3 is a cross-sectional view of the pad of the invention in the form of a cuff.

DESCRIPTION OF THE PREFERRED EMBODIMENTS

Referring first to FIG. 1, there is indicated a pad 10 which is associated with a monitor 12. The pad 10 holds one or more pH indicator means 13 which can measure the pH of fluid about the pH of blood. The pad also holds contacts 14 which become electrically connective by means of a fluid contact. The monitor 12 continuously reads both the pH and wetness.

As illustrated in FIG. 1, the monitor 12 is provided with a power supply cord 15 adapted for connection with the common 120 volt, 60 cycle power supply line. The monitor may also be provided with its own power source such as a battery in the event of a power failure. In place of the pH indicator can be used a glucose measuring device.

For the purpose of briefly explaining the several functions performed by the monitor, reference is made to FIG. 2. In this figure it will be seen that on the main panel of the monitor as shown in FIG. 2, the monitor 12 is provided with power shut-off switch 16 and also signal lights 11, 18 and 19. The first of these lights 11 is desirably of white color, and is turned on with the power switch 16 provided power is present. The second of the lights 18 which is desirably of an orange or yellow color is energized when the pH or other blood characteristic in a designated range is read. The pH range is about 7.35-7.45, which is the pH of normal blood. Other wetness such as perspiration or urine would be outside of this range. The third of these signals 19 is desirably of blue color and is energized when there is sufficient wetness to cause electrical contact between the contacts 14 or when other blood characteristics can be measured by an indicator. A reset button 20 is provided for the signal light 18 since it is possible to obtain a pH reading or other indicative blood readings within the blood range can be measured without profuse bleeding. Alternatively, the reset button could be provided for the wetness signal which could be a result of perspiration or other fluids. When both signal lights 18 and 19 are energized there is further energized visual and/or audio means 21. When means 21 is energized this means that an emergency situation has occurred wherein profuse bleeding has taken place. Similarly, a blood glucose meter can be utilized in place of the pH indicator and/or wetness indicator. In the invention the contacts 14 may be additional pH indicators which are located in the pad at a position where profuse bleeding would reach. Also, the contacts 14 may be used together with further pH indicators.

FIG. 3 shows the pad in the form of a cuff 22 which is intended to be placed around a limb or around a body portion. The cuff 22 may be provided with means for holding the cuff 22 in place. One suitable means for holding the cuff in place is velcro portions 23a and 23b. The cuff 22 contains on its surface the pH indicating means 23. A wetness indicating means 24 is placed below the surface at a distance desirable for the amount of wetness to be indicated. The distance is dependent upon the degree of absorbability of the material utilized in the cuff. The positioning of the different contacts 24 is such as required by the materials utilized and the degree of wetness determined as being critical together with other factors which may be involved with the particular patient, such as, the size and weight of patient. The differences between the amount of blood loss by an infant and an adult should be considered in the determination of blood loss. The combination of the predetermined pH and the wetness indicated will then activate the main alarm or indicator which can be a visual alarm 21 and/or an audio alarm. It can therefore be seen that the occurrence of two separate events can be essential in notifying a supervising party of the occurrence of a critical event. The indicator 24 may either be of the type activated by wetness or pH indication or blood glucose.

The purpose of the reset switch 20 being the resetting of one of the signals in the absence of two of the features existing simultaneously which would make the event critical with respect to the condition of the patient. The pilot light 14 is preferably associated with the power supply line 15 beyond the shut-off switch 19 to thereby provide a visual signal of the presence of power in the unit when the switch 16 is turned on.

If desired there may be incorporated into the pad a further feature wherein the temperature of fluid which enters the pad is immediately measured. By such a method the combination of the pH, wetness and temperature would indicate an immediate problem relating to blood loss.

As further seen in FIG. 3, a pad 22 in the form of a cuff having velcro fasteners 23a, 23b, so is adapted to encircle and be held in position on a limb or torso. Along the upper surface of the pad 22, may be a pH indicator 25 for noting initial blood loss. Below the pH indicator may be either a wetness indicator which is activated when a fluid bridge is formed between a pair of contacts 24 or a further pH indicator. The placement of the pH indicator 25 and the wetness contacts 24 or additional pH indicator is dependent upon the amount of blood loss intended before alarm, the type of materials forming the pad and the location from the blood loss area. If desired, a temperature indicator may also be utilized so as to have more than two factors to determine criticality. The temperature indicator is especially useful for immediate and prolonged blood loss indication. The pad 22 is associated with a monitor device as hereinbefore described. Amongst the suitable pH meters and glucose detection means which may be utilized are those marketed by Beckman Instruments, Inc. a subsidiary of SmithKline-Beckman, Philadelphia, Pa. The wetness contacts which may be used are disclosed in U.S. Pat. No. 2,907,844 to Kenneth E. Campbell.

In the operation of the monitor of the present invention, a patient after major surgery is supplied with the monitor of the present invention near the area of injury wherein a pad having the pH and wetness indicators or additional pH indicators are incorporated. If there is bleeding, the monitor which may be in a central location for more than one patient, is activated. If only slight bleeding occurs, ony one of the indicators is activated. This may be normal for the type of surgical procedure which the patient was submitted. However, when there is more than one indicator the criticality is better appraised by an attendant. The indicators are such that would preclude perspiration, urine, or the like which may be associated with non-surgical related events. The indicators which are mentioned relate to blood indicators which are activated where profuse blood flows. It is intended that the indicators be such which can readily be determined by known means and whose readings when combined as programmed will indicate to an attendant the criticality of the situation relating to the patient's disposition. For example, the wetness indicator need not rely upon the formation of a wetness bridge but can detect blood merely by its presence such as the occurrence of pH or glucose reading. This also means that there can be more than one indicator, that is, if the blood can be measured at different levels in the pad it is a sign of profuse bleeding which needs attention. Therefore, as provided by the present invention the indicator may be determined at different levels of penetration of blood into the pad. When more than one level in the pad measures or indicates the blood it energizes a signal which notifies an attendant of an emergency.

It is understood that it is possible to indicate a degree of wetness by being able to measure the presence of blood at different levels so as to indicate profuse blood loss. Such loss is measurable by the presence of blood through pH, blood glucose or wetness.

What is claimed is:

1. A monitor of blood loss from a patient comprising the combination of a pad having a means for detecting blood presence and means for detecting wetness which indicates wetness from blood and non-blood fluids, and means associated with said pad for indicating the presence of blood and wetness from said detecting means, and providing an electrical signal for each indication, whereby the activation of all signals indicates profuse blood loss.

2. The monitor according to claim 1 wherein said means for detecting means comprises electrical contacts which are activated by a fluid bridge formed by blood or other fluids.

3. The monitor according to claim 1 wherein said means for detecting wetness and the means for detecting blood are each pH indicators and are activated when the pH of blood can be detected.

4. The monitor of claim 3 wherein said pH indicators are placed at different positions in the pad so as to indicate a degree of fluid penetration in the pad.

5. The monitor of claim 3 including light means associated with said blood detecting means and said wetness detecting means for providing a visual signal upon activation of the blood detecting means and the wetness detecting means.

6. The monitor of claim 5 including a means associated with said blood detecting means and said wetness detecting means for providing an audio signal upon activation of the blood detecting means and the wetness detecting means.

7. The monitor of claim 1 including means for resetting signal readings which indicate the presence of wetness.

8. The monitor of claim 1 including temperature indicating means in said pad.

9. The monitor of claim 1 wherein the blood presence detecting means is a glucose measuring meter.

10. The monitor of claim 1 wherein the wetness detecting means is a glucose measuring meter.

11. The monitor of claim 1 wherein the blood presence and wetness detecting means are each glucose measuring meters.

12. A method for detecting profuse blood loss from a patient comprising providing means for measuring the presence of blood only, measuring the presence of blood at a predetermined position with said means, electrically signalling the presence of blood at said predetermined position, providing means for measuring wetness by all fluids at another predetermined position, measuring the presence of wetness with said wetness measuring means, electrically signalling the presence of wetness, and distinguishing blood wetness from other wetness from the combined signals so as to indicate profuse blood loss.

13. The method of claim 12 wherein the presence of blood at said predetermined position is electrically signalled a pH indicator.

14. A method for detecting profuse blood loss from a patient and simultaneously distinquishing blood loss from other body fluids which comprises providing a fluid absorbent pad having at a first predetermined position means for measuring the pH of blood, measuring for the pH of blood at said first position, providing signal generating means in association with said blood pH measuring means, signalling the presence of blood with said signal generating means, providing wetness indicator means at a second predetermined position in said pad for indicating wetness and signal generating means in association with said wetness indicator means, signalling wetness at said second predetermined position, whereby the simultaneously activation of the signal means for blood and the wetness indicates profuse blood loss.

15. The method of claim 12 wherein the wetness measuring means indicates the formation of an electrical fluid bridge.

16. The method of claim 12 wherein the blood presence and wetness is measured by pH.

17. A method for detecting profuse blood loss from a patient and simultaneously distinguishing blood loss from other body fluids which comprises providing a fluid absorbent pad having at a first predetermined position means for measuring the pH of blood and signal generating means associated with said blood pH measuring means for signalling the presence of blood, providing wetness indicator means at a second predetermined position in said pad for indicating wetness and signal generating means associated with said wetness indicator means for signalling wetness, whereby the simultaneously activation of the signal means for blood and the wetness indicates profuse blood loss.

* * * * *